(12) United States Patent
McCulloch

(10) Patent No.: US 9,354,010 B1
(45) Date of Patent: May 31, 2016

(54) FIREARM BREATHALYZER

(71) Applicant: Patrick McCulloch, San Francisco, CA (US)

(72) Inventor: Patrick McCulloch, San Francisco, CA (US)

(73) Assignee: Patrick McCulloch, Los Gatos, CA (US)

( * ) Notice: Subject to any disclaimer, the term of this patent is extended or adjusted under 35 U.S.C. 154(b) by 0 days.

(21) Appl. No.: 14/885,692

(22) Filed: Oct. 16, 2015

(51) Int. Cl.
*F41A 17/06* (2006.01)
*G01N 33/497* (2006.01)

(52) U.S. Cl.
CPC ............ *F41A 17/06* (2013.01); *G01N 33/4972* (2013.01)

(58) Field of Classification Search
CPC ..... F41A 17/06; F41A 17/063; F41A 17/066; F41A 17/08; F41A 17/30; F41A 17/46
USPC ............ 42/70.11, 84, 70.01, 70.07, 70.06, 66
See application file for complete search history.

(56) References Cited

U.S. PATENT DOCUMENTS

| | | |
|---|---|---|
| 4,457,091 A | 7/1984 | Wallerstein |
| 5,220,919 A | 6/1993 | Phillips |
| 5,570,528 A | 11/1996 | Teetzel |
| 5,675,925 A | 10/1997 | Wurger |
| 5,713,149 A | 2/1998 | Cady |
| 6,223,461 B1 | 5/2001 | Mardirossian |
| 6,293,039 B1 | 9/2001 | Fuchs |
| 6,301,815 B1 | 10/2001 | Sliwa |
| 6,314,671 B1 | 11/2001 | Gering |
| 6,321,478 B1 | 11/2001 | Klebes |
| 6,481,140 B1 | 11/2002 | Marshall |
| 6,711,844 B2 | 3/2004 | Rumfelt |
| 6,735,897 B1 | 5/2004 | Schmitter |
| 6,823,621 B2 | 11/2004 | Gotfried |
| 7,600,339 B2 | 10/2009 | Schumacher |
| 7,703,229 B2 | 4/2010 | Parhofer |
| 7,934,577 B2 | 5/2011 | Walter |
| 8,127,482 B2 | 3/2012 | O'Shaughnessy |
| 8,418,391 B2 | 4/2013 | Kemmerer |
| 8,756,850 B2 | 6/2014 | Dietel |
| 8,931,195 B2 | 1/2015 | Milde, Jr. |
| 8,966,797 B2 * | 3/2015 | Carlson ................. F41A 17/063 42/1.01 |
| 2001/0032405 A1 | 10/2001 | Kaminski |
| 2001/0042332 A1 | 11/2001 | Gering |
| 2004/0099134 A1 | 5/2004 | Gotfried |
| 2006/0182661 A1 | 8/2006 | Aquila |

(Continued)

OTHER PUBLICATIONS

"How well could one attach a breathalyzer to a gun's trigger-lock?" Answers.yahoo.com, published on or before Dec. 20, 2012, retrieved May 28, 2015, https://answers.yahoo.com/question/index?qid=20121220141213 AA4pwwU, 2 pages.

(Continued)

*Primary Examiner* — Joshua Freeman
(74) *Attorney, Agent, or Firm* — Fish & Richardson P.C.

(57) ABSTRACT

A system for locking a firing mechanism of a firearm in response to blood-alcohol content can include a breathalyzer system and a lock system. The breathalyzer system can be configured to connect to a firearm and include an input port for receiving fluid and a processing module for analyzing blood-alcohol content of the fluid. The lock system can be configured to connect to the firearm and be operably connected to the breathalyzer system for receiving a signal from the breathalyzer system so as to disable a firing mechanism of the firearm in response to the blood-alcohol content of the fluid being sensed to be above a threshold.

18 Claims, 6 Drawing Sheets

(56) References Cited

U.S. PATENT DOCUMENTS

| | | |
|---|---|---|
| 2006/0242879 A1 | 11/2006 | Schmitter |
| 2007/0074438 A1 | 4/2007 | Parhofer |
| 2007/0180749 A1 | 8/2007 | Schumacher |
| 2009/0223104 A1 | 9/2009 | Anzeloni |
| 2011/0030262 A1 | 2/2011 | O'Shaughnessy |
| 2013/0021153 A1* | 1/2013 | Keays ............... G01N 33/4972 340/539.12 |
| 2013/0167423 A1 | 7/2013 | Lupher |
| 2014/0173961 A1 | 6/2014 | Goren |
| 2014/0215881 A1 | 8/2014 | Milde, Jr. |
| 2014/0215882 A1 | 8/2014 | Milde, Jr. |
| 2014/0215883 A1* | 8/2014 | Milde, Jr. ............... F41A 35/00 42/70.11 |
| 2014/0230301 A1 | 8/2014 | Chance |
| 2014/0259841 A1* | 9/2014 | Carlson ............... F41A 17/063 42/1.01 |
| 2014/0335905 A1* | 11/2014 | Bhoot ............... H04W 4/02 455/466 |
| 2015/0153124 A1* | 6/2015 | Carlson ............... F41A 17/063 42/70.02 |
| 2015/0184963 A1* | 7/2015 | Milde, Jr. ............... F41A 17/066 42/70.06 |
| 2015/0226727 A1* | 8/2015 | Son ............... G01N 33/0008 73/23.3 |

OTHER PUBLICATIONS

"BreathKey g10 Keychain Breathalyzer," BreathKey, retrived May 28, 2015, http://www.breathkey.com/breathkey-g10-keychain-breathalyzer, 2 pages.

"How They Work," BreathKey, retrieved May 28, 2015, http://www.breathkey.com/how-it-works, 2 pages.

"Intelligun. It's your gun." Intelligun, retrieved on May 28, 2015, http://www.intelligun.com/, 2 pages.

* cited by examiner

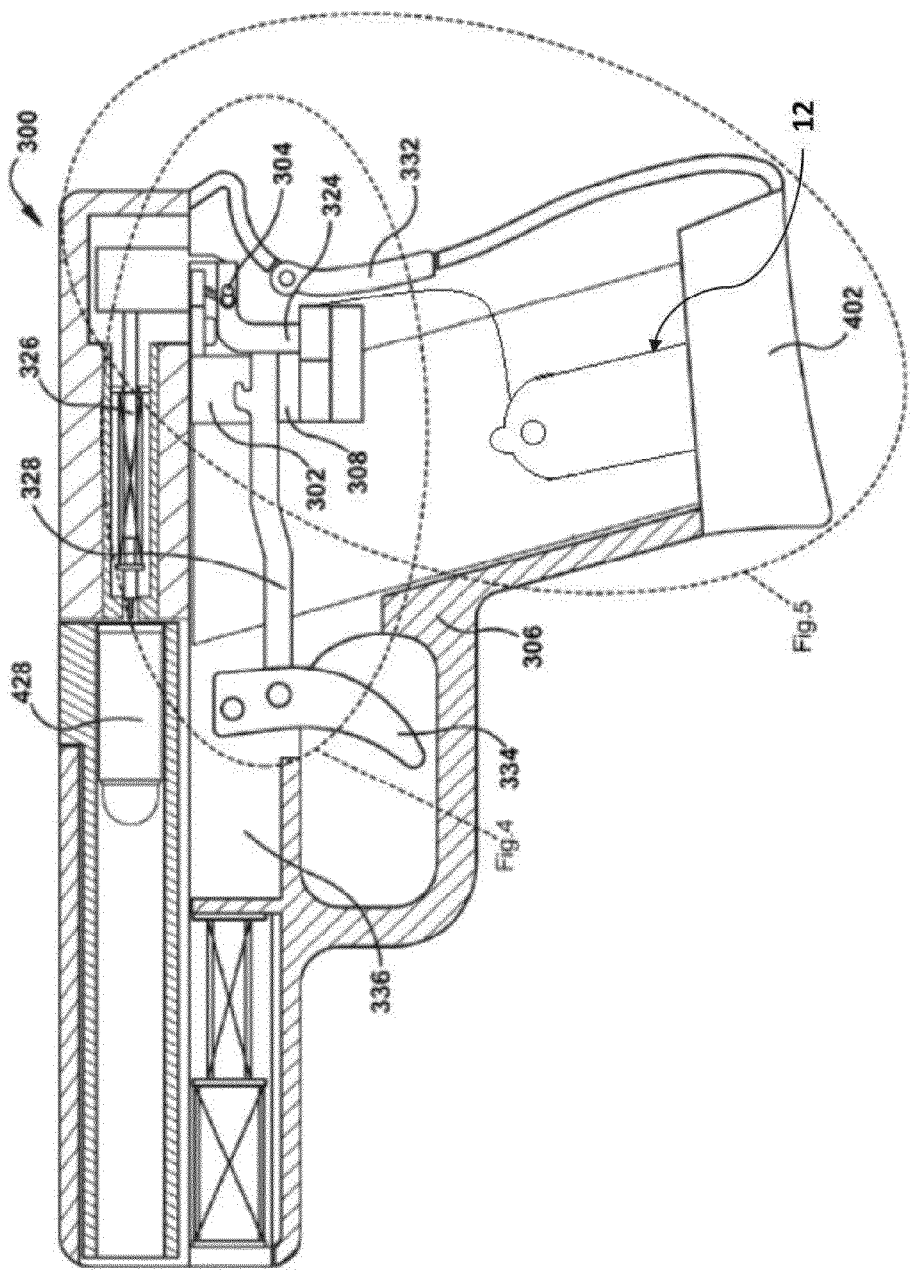

FIREARM BREATHALYZER

TECHNICAL FIELD

This invention relates to firearms, and more particularly to firearm safety.

BACKGROUND

Firearms, or more commonly called guns, can be used for many purposes. Some of these purposes can include hunting, law enforcement, and self-defense, and military use. In some cases, firearms can be dangerous when used improperly by the user.

SUMMARY

Some embodiments of a breathalyzer system can include one or more of the features and functions disclosed herein. Some embodiments can include a firearm having an integrated breathalyzer that can disable and enable the breathalyzer in response to sensed blood-alcohol content (BAC). Some embodiments can include a lock system that locks a firing mechanism in response to being signaled by the breathalyzer system. Some embodiments can improve firearm safety by reducing or preventing operation of the firearm by an intoxicated individual. Implementations can include any, all, or none of the following features.

In one aspect, a firearm can include a firing mechanism, a breathalyzer system, and a lock system. The breathalyzer system can include an input port for receiving fluid (such as breath) and a processing module for analyzing blood-alcohol content of the fluid. The lock system can be operably connected to the firing mechanism and operably connected to the breathalyzer system for receiving a signal from the breathalyzer system so as to disable the firing mechanism of the firearm in response to the blood-alcohol content of the fluid being sensed to be above a threshold.

Implementations can include any, all, or none of the following features. The lock system enables the firing mechanism of the firearm in response to the blood-alcohol content of the fluid being sensed to be below the threshold. The lock system is biased in a locked position such that the firing mechanism is disabled if a user does not first blow into the input port of the breathalyzer system. The lock system enables the firing mechanism of the firearm in response to the blood-alcohol content of the fluid being sensed to be below the threshold for a period of time and then locks the firing mechanism after the period of time expires. The firearm is a handgun comprising a grip defining a magazine well and a breathalyzer receptacle positioned adjacent the magazine well. The input port is positioned on a side of a grip of the firearm and is configured for receiving a blowing straw in which a user can blow. At least parts of both the breathalyzer and the lock system are positioned in a grip of the firearm. The breathalyzer system and the lock system are operably connected to the firearm so as to enable and disable a safety mechanism of the firearm in response to sensed BAC.

In one aspect, a system for locking a firing mechanism of a firearm in response to blood-alcohol content can include a breathalyzer system and a lock system. The breathalyzer system can be configured to connect to a firearm and include an input port for receiving fluid and a processing module for analyzing blood-alcohol content of the fluid. The lock system can be configured to connect to the firearm and be operably connected to the breathalyzer system for receiving a signal from the breathalyzer system so as to disable a firing mechanism of the firearm in response to the blood-alcohol content of the fluid being sensed to be above a threshold.

Implementations can include any, all, or none of the following features. The lock system is configured to enable the firing mechanism of the firearm in response to the blood-alcohol content of the fluid being sensed to be below the threshold. The lock system is configured to be biased in a locked position such that the firing mechanism would be disabled if a user does not first blow into the input port of the breathalyzer system. The lock system is configured to enable the firing mechanism of the firearm in response to the blood-alcohol content of the fluid being sensed to be below the threshold for a period of time and then lock the firing mechanism after the period of time expires. The breathalyzer system is sized to be positioned in a receptacle adjacent a magazine well. The breathalyzer system and the lock system are configured to be connected to the firearm so as to enable and disable a safety mechanism of the firearm in response to sensed BAC.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a schematic side sectional view of one embodiment of a firearm having a lock system for use with the breathalyzer system.

Like reference symbols in the various drawings indicate like elements.

DETAILED DESCRIPTION

Figure 1:
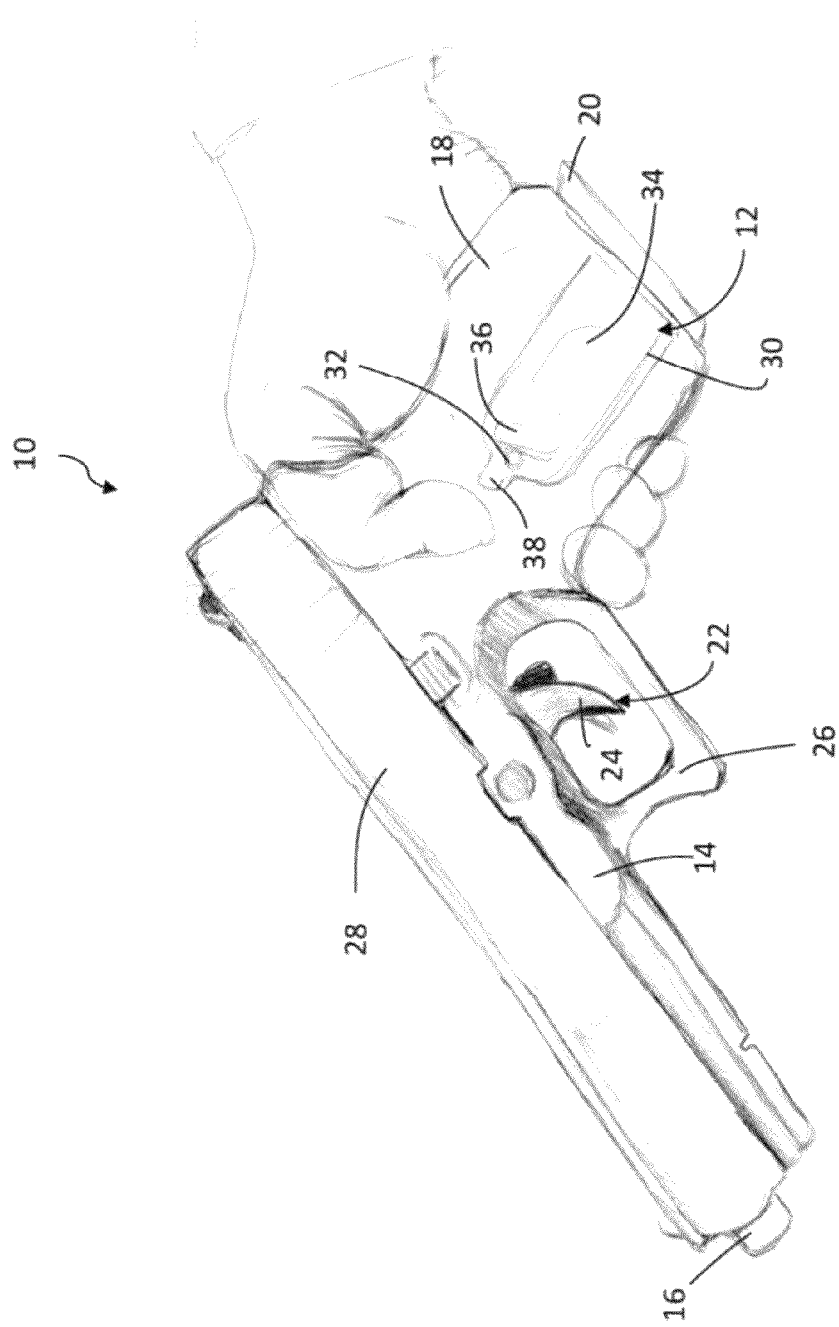
FIG. 1 is a side view of a firearm having a breathalyzer system.

FIG. 1 is a side view of a firearm 10, commonly called a gun, having a breathalyzer system 12 connected thereto. The firearm 10 includes a frame 14, a barrel 16, a grip 18 (also called a handle), a magazine 20, a firing mechanism 22 including a trigger 24, a trigger guard 26, and a slide 28. In the illustrated embodiment, the firearm 10 is a semi-automatic pistol. In various embodiments, the firearm 10 can be other embodiments of handguns. In other embodiments, the firearm 10 can be other types of guns suitable for the application, such as long range rifles, shotguns, and carbines, revolvers, and other manual, semi-automatic, and automatic firearms, including those for hunting, personal defense, and military use.

The breathalyzer system 12 is operably connected to the firearm 10 to enable and disable operation of the firearm 10 in response to blood-alcohol content (BAC) of the user. In some embodiments, the breathalyzer system 12 can be operably connected to the firing mechanism 22. The breathalyzer system 12 can enable the firing mechanism 22 when the user blows into the breathalyzer system 12 with a BAC below a threshold and can disable the firing mechanism 22 when the user blows into the breathalyzer system 12 with a BAC that is above the threshold.

The breathalyzer system 12 can be configured to disable the firing mechanism 22 as a default, such that the firing mechanism 22 is disabled if no user blows into the breathalyzer system 12. In such embodiments, the breathalyzer system 12 enables operation of the firing mechanism 22 and the firearm 10 only after a user blows into the breathalyzer system 12 and only if the BAC is below the threshold.

The breathalyzer system 12 can be configured to prevent or reduce the risk of a user operating the firearm 10 with a BAC over the threshold. The threshold can be set to a level to prevent or reduce the risk of operation while intoxicated, such as to the same level as used by government agencies in motor vehicle regulations. In some embodiments, the threshold can be set to a BAC of 0.08%. In some embodiments, the threshold can be set to a BAC that is lower than 0.08%. In such embodiments, operation of the firearm 10 can be limited to users with a BAC that is even lower than the BAC limit allowed for motor vehicle operation in many jurisdictions. For example, the threshold can be set to a BAC of 0.04%. Alternatively, the threshold can be set to a BAC of 0.01% or even less. In some embodiments, the threshold can be set to substantially no BAC.

In some embodiments, the breathalyzer system 12 can be configured with multiple BAC threshold settings, such as having a default BAC threshold and also being adjustable to a more restrictive BAC threshold. For example, the threshold can be set to a BAC of 0.08% as a default that is adjustable to levels less than 0.08%. This can allow a user to set the threshold to a BAC that the user is more comfortable with, such as 0.07%, 0.04%, or 0.01%.

In some embodiments, the breathalyzer system 12 can include a housing 30 and an input port 32 for receiving fluid (such as breath of the user) into the housing 30 of the breathalyzer system 12 for analysis of the BAC of the fluid. In some embodiments, the breathalyzer system 12 can also include a user interface 34 which can include one or more input buttons 36. The user interface 34 can include a display, such as a liquid crystal display (LCD) for displaying information to a user. Information displayed to the user can include information associated with the breathalyzer system 12, such as sensed BAC, threshold BAC, and/or other settings and user preferences. The user interface 34 can include a touch screen display with the buttons 36 embedded in the display or the buttons 36 can be separate from the display, as illustrated in FIG. 1.

In some embodiments, the breathalyzer system 12 can be physically attached to the firearm 10, such as attached to the frame 14 or the grip 18. For example, the breathalyzer system 12 can be positioned in a breathalyzer receptacle that is defined by the grip 18, and can be positioned adjacent a magazine well also defined by the grip 18 and configured for receiving the magazine 20.

The breathalyzer system 12 can be attached to the firearm 10 via one or more fasteners. For example, in some embodiments, the breathalyzer system 12 can have a fastening feature 38 configured for fastening the breathalyzer system 12 to the firearm 10. In various embodiments, the breathalyzer system 12 can be fastened to the firearm 10 by one or more screws, bolts, snaps, brackets, adhesives, or other fasteners suitable for the application.

In some embodiments the breathalyzer system 12 can be positioned on an exterior surface of the firearm 10 (such as an exterior surface of the grip 18). In some of such embodiments, the user interface 34 can be positioned for easy access by a user. In some embodiments, the breathalyzer system 12 can be positioned in an interior cavity of the firearm 10 (such as an interior receptacle of the grip 18). In some of such embodiments, the user interface 34 can be omitted. In embodiments having the breathalyzer system 12 positioned in an interior cavity of the firearm 10, the input port 32 can be fluidically connected to an exterior of the firearm 10 so as to allow a user to blow into the input port 32 of the breathalyzer system 12.

In some embodiments, the input port 32 can be positioned on the firearm 10 on the grip 18 of the firearm 10, such as on the side of the grip 18 (as illustrated in FIG. 1) or on the rear of the grip 18. In other embodiments, the input port 32 can be positioned at another location on the firearm 10 suitable for the application.

In some embodiments, the breathalyzer system 12 can be modified to sense BAC in other bodily fluids, such as perspiration. In such embodiments, the system 12 can be positioned in contact with a hand of the user (such as on the grip 18) and can sense secretions from the user's hand for enabling and disabling the firearm 10.

In some embodiments, substantially all components of the breathalyzer system 12 are positioned on the firearm 10. In other embodiments, one or more components of the breathalyzer system 12 can be separate from other components of the breathalyzer system 12 that are on the firearm 10. In such embodiments, various components of the breathalyzer system 12 can communicate via a wired connection or via a wireless connection (such as, for example, via a Bluetooth wireless connection or other suitable communication mechanism). In the various embodiments, the breathalyzer system 12 can be configured to enable and disable the firing mechanism 22 in response to sensed BAC of the user.

Figure 2A:
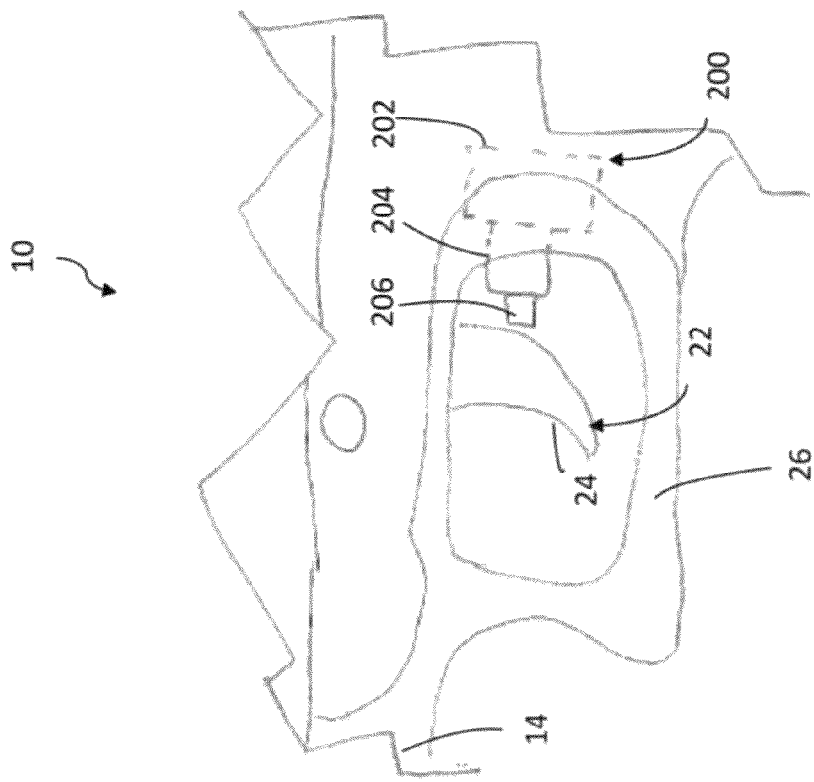
FIG. 2A is an enlarged view of a firing mechanism of the firearm of FIG. 1.

FIG. 2A is an enlarged view of the firing mechanism 22 of the firearm 10, shown with one embodiment of a lock system 200. The lock system 200 can be connected to and/or part of the breathalyzer system 12 (shown in FIG. 1). The lock system 200 can be operably connected to the firing mechanism 22 and operably connected to the breathalyzer system 12 for receiving a signal from the breathalyzer system 12 so as to disable the firing mechanism 22 of the firearm 10 in response to the BAC of the fluid being sensed by the breathalyzer system 12 to be above a threshold.

The lock system 200 can be actuated between a locked position whereby the firing mechanism 22 is restricted from firing and an unlocked position whereby the firing mechanism 22 is permitted to fire. In some embodiments, the lock system 200 can include an actuator 202, a mechanism 204, and an engagement member 206. The actuator 202 can be connected to the engagement member 206 via the mechanism 204 for driving the engagement member 206 between engaged and disengaged positions. In the engaged position, the engagement member 206 can engage a portion of the firing mechanism 22 (such as the trigger 24) to lock the firing mechanism 22. In the disengaged position, the engagement member 206 can disengage from the portion of the firing mechanism 22 (such as the trigger 24) to unlock the firing mechanism 22, and consequently, allow full motion of the firing mechanism 24 including the trigger 24. In some embodiments, the actuator 202 can include a solenoid and the engagement member 206 can include a pin driven by the solenoid. In some embodiments, the actuator 202 can include another motor suitable for the application of locking and unlocking the firing mechanism 22.

In other embodiments, the lock system 200 can be modified differently than as illustrated to mechanically and/or electrically enable and disable the firing mechanism 22. For example, in some embodiments the lock system 200 can electrically enable and disable the firing mechanism by closing and opening an electrical circuit that is part of the system.

Figure 2B:
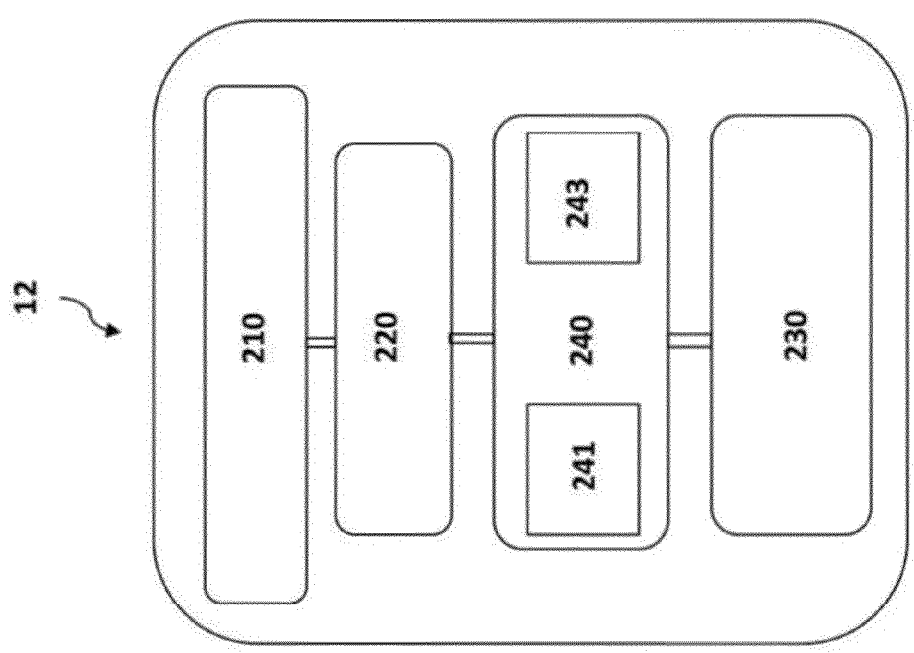
FIG. 2B is a schematic view of one embodiment of the breathalyzer system of FIG. 1.

FIG. 2B is a schematic view of one embodiment of the breathalyzer system 12, which can include a sample receiving module 210 configured to accept breath samples of the user received at the input port 32; a sample processing module 220 configured to analyze the breath samples; a storage module 230 configured to store and/or transmit data; and an electronics subsystem 240 comprising a power module 241 configured to power the sample processing module 220 and a conditioning module 243 configured to process signals generated by a sensor of the sample processing module 220.

The sample receiving module 210 defines a cavity configured to accept the set of breath samples of the user, and functions to provide a module that facilitates reception and processing of the set of breath samples.

The sample processing module 220 is configured to couple to the cavity of the sample receiving module 210, and functions to facilitate analysis of the breath samples and generation of signals from the breath samples. As such, the sample processing module 220 preferably includes one or more sensors coupled to the electronics subsystem 240, wherein the sensor interacts with a sample of the set of breath samples and the electronics subsystem 240 conditions signals produced based upon the sensor-sample interaction for transmission to a processor for further analysis. The sample processing module 220 is preferably housed within the sample receiving module 210, but can alternatively be configured relative to the sample receiving module 210 in any other suitable manner. The sample processing module 220 can sense via a fuel cell sensor that enables measurement of a user's BAC by an electrochemical process or by a semiconductor sensor that produces a change in electrical resistance in response to an alcohol-dioxide reaction, wherein the magnitude of the change in resistance varies in a predictable manner according to the amount (e.g., relative volume) of alcohol carried in the breath sample. The sample processing module 220 can, alternatively, include any other suitable elements that facilitate sample processing and transmission.

The electronics subsystem 240 can include the power module 241 configured to power the sample processing module 220 and the conditioning module 243 configured to process signals generated by the one or more sensors for transmission and further analysis. As such, the electronics subsystem 240 functions to provide power to elements of the breathalyzer system 12, condition and/or preprocess signals generated from received breath samples, and facilitate transmission of signals to a processor for further analysis.

The power module 241 of the electronics subsystem 240 can provide electrical power to the sample processing module 220 and to allow power storage for the sample processing module 220. The power module 241 can comprise a battery, such as a lithium-ion battery that is configured to be rechargeable, but can alternatively comprise any other suitable rechargeable battery (e.g., nickel-cadmium, metal halide, nickel metal hydride, or lithium-ion polymer). Alternatively, the power module 241 can comprise a non-rechargeable battery (e.g., alkaline battery) that can be replaced.

The conditioning module 243 can preprocess signals generated by a sensor prior to transmission from the sample processing module 220, and can additionally regulate elements of the electronics subsystem 240. The conditioning module can include signal conditioning elements, including one or more of: an analog-to-digital converter, an amplifier, and a filter for processing signals prior to transmission. In some embodiments, the conditioning module 243 can include a microprocessor configured to direct signal conditioning functionalities of the conditioning module 243 and a voltage regulator configured to protect elements of the electronics subsystem 240 from overvoltage and/or under-voltage states.

The output of the sample processing module 220 of the breathalyzer system 12 can be a BAC level (e.g. 0.08% or 0.01%), can be a pass/no-pass signal, or can be a different signal suitable for the application. In any case, the breathalyzer system 12 can output a signal configured to drive a lock system (such as lock system 200, shown in FIG. 2A) to lock a firing mechanism 22 of the firearm 10 (shown in FIG. 1). In other embodiments, the breathalyzer system 12 can have addition components or be otherwise configured as suitable for the application.

FIG. 3 is a schematic side sectional view of one embodiment of a firearm 300 having a lock system 304 for use with the breathalyzer system 12. The firearm 300 can be similar to the firearm 10 (shown in FIGS. 1 and 2) and can include much of the components of the firearm 10, including the breathalyzer system 12. The breathalyzer system 10 can be connected to the lock system 304 in wired or wireless communication. The lock system 304 can be operably connected to the breathalyzer system 12 for receiving a signal from the breathalyzer system 12 so as to disable firing of the firearm 300 in response to the BAC of the fluid being sensed by the breathalyzer system 12 to be above a threshold.

In some embodiments, the lock system 304 can include a computer processing unit 302, such as a microprocessor. Both the computing processing unit 302 and the lock system 304 can be located within and/or secured to a frame 306 of the firearm 300. The lock system 304 can operate in various manners depending upon the type of firearm being utilized, such as a pistol, rifle, etc. The lock system 304 can be of any appropriate shape, size, type or configuration, such as a bar, L-shaped bar, and the like, depending upon the desired location of the lock system in the desired type of firearm. The microprocessor 302 may lock down the firearm 300 via the lock system 304 in conjunction with the breathalyzer system 12.

The lock system 304 can be located in any appropriate location on the frame 306 of the firearm 300, depending upon where the lock system 304 can best fit. In the illustrated embodiment of FIG. 3, the firearm 300 can include a semi-automatic pistol, for example.

Figure 4:
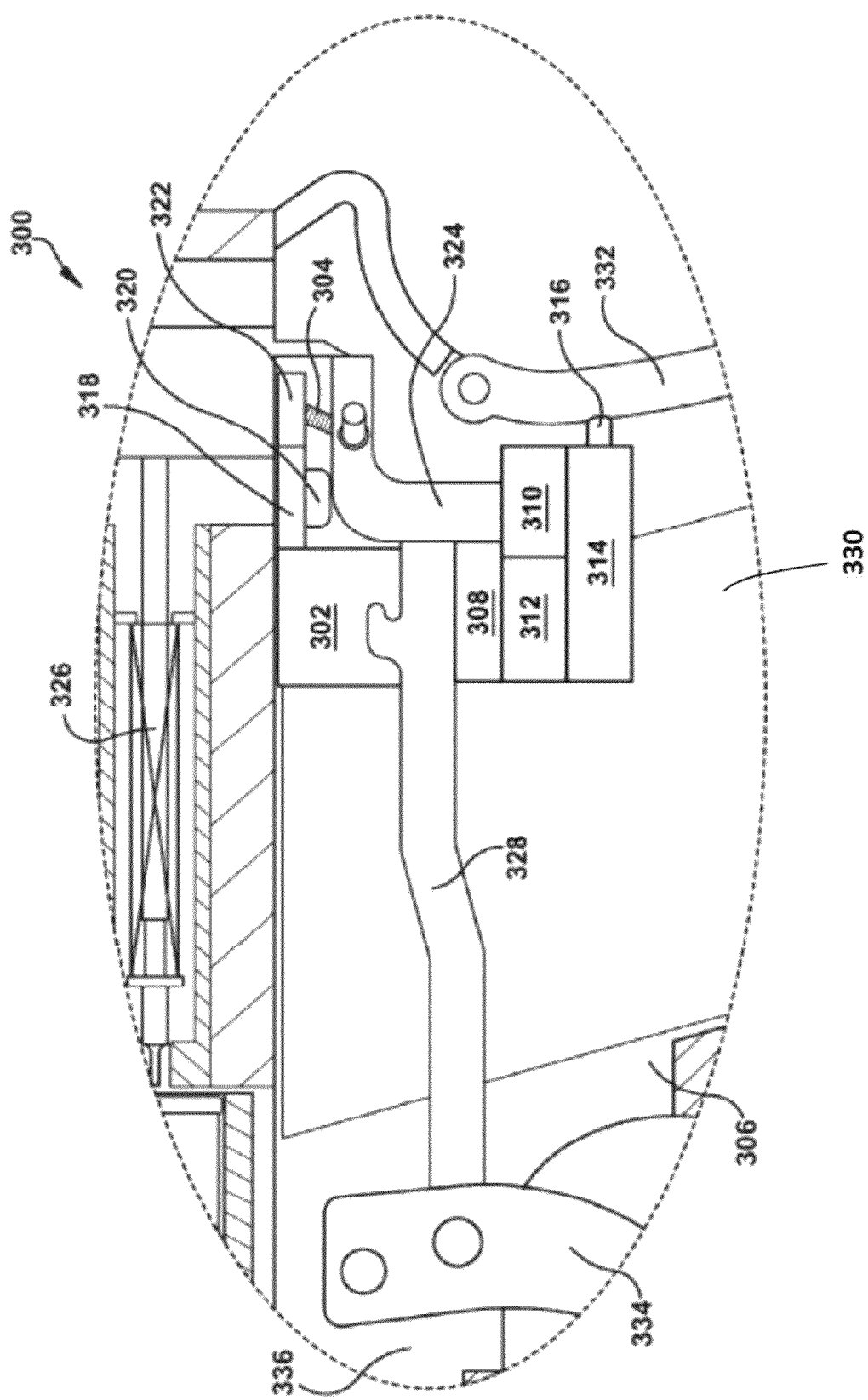
FIG. 4 shows an enlarged side sectional view of the lock system of FIG. 3.

FIG. 4 shows an enlarged side sectional view of the lock system 304 of FIG. 3. As shown in FIG. 4, the lock system 304 can include various electronic components, such as a microprocessor 302, a memory 308, a transmitter 310, a receiver 312, a battery 314 and an input port 316, such as for charging the battery 314 if needed. The firearm 300 can also include a switch 318, a relay 320 and a motor 322 connected to the lock system 304.

In use, the microprocessor 302 can receive a signal to lock down the firearm 300 and the lock system 304 can move into the lock position. As shown in FIG. 4, the firearm 300 can be locked down via the lock system 304 by preventing a sear 324 from moving a striker 326. The sear 324 of the firearm can be locked, thereby preventing the striker 326 from making contact with a cartridge primer of a round 428 (shown in FIG. 3). A trigger lock bar 328 can be housed in a grip 330 of the firearm 300 preventing the trigger bar 328 from moving the sear 324, which would lock the striker 326.

When the breathalyzer system 12 (shown in FIG. 3) senses BAC above a threshold, the breathalyzer system 12 can communicate with the microprocessor 302 of the lock system 304 (via a wired or wireless connection with the transmitter 310 and receiver 312) to send a signal to lock the lock system 304. The microprocessor 302 can then send a signal to drive the motor 322 to actuate the lock system to the locked position, thereby preventing the striker 326 from making contact with a cartridge primer of a round 428.

When the breathalyzer system 12 (shown in FIG. 3) senses BAC below a threshold, the breathalyzer system 12 can communicate with the microprocessor 302 of the lock system 304 (via a wired or wireless connection with the transmitter 310 and receiver 312) to send a signal to unlock the lock system 304. The microprocessor 302 can then send a signal to drive the motor 322 to actuate the lock system to the unlocked position, thereby allowing the striker 326 to make contact with a cartridge primer of the round 428, but only in response to normal activation of the firearm 300 such as by pulling a trigger 334.

In some embodiments, the lock system 304 can be biased in a locked position such that firing is disabled (e.g. the striker 326 is not allowed to make contact with a cartridge primer of the round 428) if a user does not first blow into the input port of the breathalyzer system 12. In such embodiments, the firearm 300 can be effectively inoperable until the breathalyzer system 12 receives a suitable breath sample that is below a designated BAC threshold.

In some embodiments, the lock system 304 can enable a firing mechanism of the firearm 300 in response to the BAC of the fluid being sensed to be below the threshold for a period of time and then locks the firing mechanism after the period of time expires.

Figure 5:
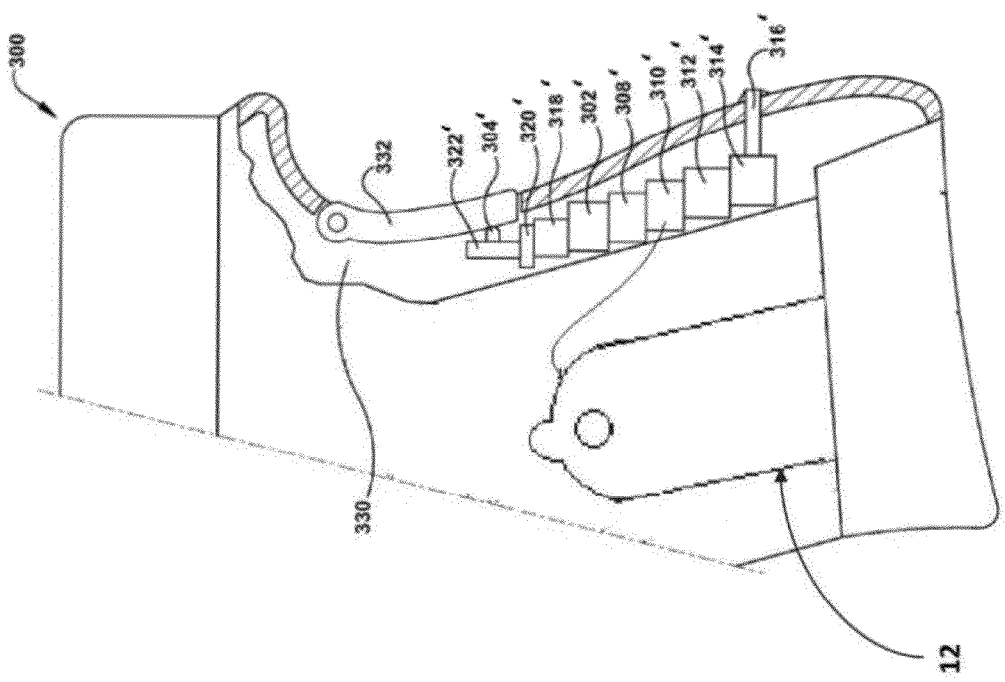
FIG. 5 is a schematic side sectional view of a portion of the grip of the firearm from FIG. 3 showing an alternative embodiment of the lock system.

FIG. 5 is a schematic side sectional view of a portion of the grip of the firearm 300 from FIG. 3 showing a lock system 304', which is an alternative embodiment of the lock system 304. The location of a lock system can depend on the make, model and caliber size of the firearm. In some embodiments, the lock system 304' can suitably engage and lock a safety of the firearm 300, such as grip safety 322. As shown in FIG. 5, the firearm 300 can include various electronic components positioned in the grip 330, such as a microprocessor 302', a memory 308', a transmitter 310', a receiver 312', a battery 314' and an input port 316', such as for charging the battery 314' if needed. The firearm 300 can also include a switch 318', a relay 320' and a motor 322' connected to a lock system 304'.

As illustrated in FIG. 5, the remote lock system 304 can be placed at a point where a bar can prevent the grip safety 332 from depressing, which can render the firearm inoperable. In another exemplary embodiment, the lock system 304 can be placed in an area closer to the trigger 334 in a configuration similar to that shown in FIG. 2A.

Some embodiments of the systems described above can have one or more benefits or advantages. For example, firearms that have a breathalyzer locking system can reduce or prevent use of those firearms by intoxicated users. This can allow users a choice to purchase a firearm having a breathalyzer locking system who would benefit from doing so. Some users, for example, might make a decision while the user is sober that he or she should not have access to a firearm while intoxicated. However, that same user may know that he or she makes different decisions when intoxicated, and may choose to operate a firearm while intoxicated. That user can purchase a firearm having a breathalyzer locking system to ensure safety for himself or herself (and possibly others) in anticipation of future intoxication. This can reduce alcohol-related gun injuries, including homicides, suicides, domestic violence, and accidental discharges, while still allowing many of the benefits of firearm ownership while sober. The safety benefit for the public at large would increase with widespread public use.

A number of embodiments of the invention have been described. Nevertheless, it will be understood that various modifications may be made without departing from the spirit and scope of the invention. For example, the firearm 10 is shown with specific components and features; however, the breathalyzer system 12 can be connected to and used with different firearms that do not include all of the components and features as disclosed with the firearm 10. The breathalyzer system 12 can be connected to such firearms to electrically and/or mechanically enable and disable the firearm in response to blood-alcohol content as disclosed herein. Accordingly, other embodiments are within the scope of the following claims.

What is claimed is:

1. A firearm handgun comprising:
a firing mechanism;
a grip defining a magazine well;
a breathalyzer receptacle positioned adjacent the magazine well;
a breathalyzer system comprising an input port for receiving fluid and a processing module for analyzing blood-alcohol content of the fluid; and
a lock system operably connected to the firing mechanism and operably connected to the breathalyzer system for receiving a signal from the breathalyzer system so as to disable the firing mechanism of the firearm in response to the blood-alcohol content of the fluid being sensed to be above a threshold.

2. The firearm of claim 1, wherein the lock system enables the firing mechanism of the firearm in response to the blood-alcohol content of the fluid being sensed to be below the threshold.

3. The firearm of claim 2, wherein the lock system is biased in a locked position such that the firing mechanism is disabled if a user does not first blow into the input port of the breathalyzer system.

4. The firearm of claim 1, wherein the lock system enables the firing mechanism of the firearm in response to the blood-alcohol content of the fluid being sensed to be below the threshold for a period of time and then locks the firing mechanism after the period of time expires.

5. The firearm of claim 1, wherein at least parts of both the breathalyzer and the lock system are positioned in a grip of the firearm.

6. The firearm of claim 1, wherein the breathalyzer system and the lock system are operably connected to the firearm so as to enable and disable a safety mechanism of the firearm in response to sensed BAC.

7. A firearm comprising:
a firing mechanism;
a breathalyzer system comprising an input port for receiving fluid and a processing module for analyzing blood-alcohol content of the fluid; and
a lock system operably connected to the firing mechanism and operably connected to the breathalyzer system for receiving a signal from the breathalyzer system so as to disable the firing mechanism of the firearm in response to the blood-alcohol content of the fluid being sensed to be above a threshold, wherein the input port is positioned on a side of a grip of the firearm and is configured for receiving a blowing straw in which a user can blow.

8. The firearm of claim 7, wherein the firearm is a handgun comprising the grip defining a magazine well and a breathalyzer receptacle positioned adjacent the magazine well.

9. The firearm of claim 7, wherein at least parts of both the breathalyzer and the lock system are positioned in the grip of the firearm.

10. The firearm of claim 7, wherein the lock system enables the firing mechanism of the firearm in response to the blood-alcohol content of the fluid being sensed to be below the threshold.

11. The firearm of claim 10, wherein the lock system is biased in a locked position such that the firing mechanism is disabled if a user does not first blow into the input port of the breathalyzer system.

12. The firearm of claim 7, wherein the lock system enables the firing mechanism of the firearm in response to the blood-alcohol content of the fluid being sensed to be below the threshold for a period of time and then locks the firing mechanism after the period of time expires.

13. The firearm of claim 7, wherein the breathalyzer system and the lock system are operably connected to the firearm so as to enable and disable a safety mechanism of the firearm in response to sensed BAC.

14. A system for locking a firing mechanism of a firearm in response to blood-alcohol content, the system comprising:
   a breathalyzer system sized to be positioned in a receptacle adjacent a magazine well, configured to connect to a firearm, and comprising an input port for receiving fluid and a processing module for analyzing blood-alcohol content of the fluid; and
   a lock system configured to connect to the firearm and operably connected to the breathalyzer system for receiving a signal from the breathalyzer system so as to disable a firing mechanism of the firearm in response to the blood-alcohol content of the fluid being sensed to be above a threshold.

15. The system of claim 14, wherein the lock system is configured to enable the firing mechanism of the firearm in response to the blood-alcohol content of the fluid being sensed to be below the threshold.

16. The system of claim 15, wherein the lock system is configured to be biased in a locked position such that the firing mechanism would be disabled if a user does not first blow into the input port of the breathalyzer system.

17. The system of claim 14, wherein the lock system is configured to enable the firing mechanism of the firearm in response to the blood-alcohol content of the fluid being sensed to be below the threshold for a period of time and then lock the firing mechanism after the period of time expires.

18. The system of claim 14, wherein the breathalyzer system and the lock system are configured to be connected to the firearm so as to enable and disable a safety mechanism of the firearm in response to sensed BAC.

* * * * *